United States Patent [19]

Clark, III

[11] 4,186,731
[45] Feb. 5, 1980

[54] TOPICAL THERMOGRAPH

[76] Inventor: William T. Clark, III, Number Six Davis Blvd., New Orleans, La. 70121

[21] Appl. No.: 905,849

[22] Filed: May 15, 1978

[51] Int. Cl.² ............................................. A61B 5/00
[52] U.S. Cl. .................................................. 128/736
[58] Field of Search ...... 128/2 H, 2 A, 2 R, 416–418; 73/356

[56] References Cited

U.S. PATENT DOCUMENTS

| | | | |
|---|---|---|---|
| 1,662,446 | 3/1928 | Wappler | 128/416 |
| 1,889,271 | 11/1932 | Zerne | 128/416 |
| 3,114,836 | 12/1963 | Fergason et al. | 128/2 H |
| 3,812,861 | 5/1974 | Peters | 128/416 |
| 3,817,253 | 6/1974 | Gonser | 128/416 |
| 3,970,074 | 7/1976 | Mogos et al. | 128/2 H |
| 4,135,497 | 1/1979 | Meyers | 128/2 H |

Primary Examiner—William E. Kamm
Attorney, Agent, or Firm—Littlepage & Webner

[57] ABSTRACT

Opposite edges of a flexible sheet of thermographic material are held so that when the surface of the sheet is forced against a body surface, resultant opposing forces applied to the opposite edges of the sheet press all the engaging surfaces against the body surface with substantially uniform pressure.

8 Claims, 11 Drawing Figures

TOPICAL THERMOGRAPH

FIELD OF INVENTION

Surgery, Diagnostic, Temperature detectors

PRIOR ART

Goldberg et al U.S. Pat. No. 3,533,399; Flam U.S. Pat. No. 3,661,142; Nosari U.S. Pat. No. 3,998,210; Navato U.S. Pat. No. 4,030,482; and Shaw IV U.S. Pat. No. 4,043,324

OBJECTS

The technique of thermoimaging by applying plastic sheets coated with microencapsulated liquid crystals is well known. The microcapsule coatings contain families of liquid crystals which reflect light of varying color according to thermoexcitation in specific temperature ranges. The sheets permit measurement of temperature with relative accuracy, but inaccuracies occur due to the tendency of the sheets not to conform with the convolutions or hills and dales of body surfaces, either resulting in no contact at all of the sheet surface against a portion of a body surface, or in uneven pressure of this sheet surface against all the contacted body surfaces so that a non-uniform transference of heat between the body surface and the sheet surface occurs, thereby creating a false temperature reading. The object of this invention is to provide a thermographic sheet holder such that when the sheet is pressed against a body surface, the sheet is either wrapped around or flexed against the body surface with substantially uniform pressure. More specifically, where the sheet is to be applied over a convex body surface, it is maintained under tension between opposite edges so that it wraps over the convex body surface; and when the sheet is to be applied against a concave body surface, it is maintained under compression between opposite edge portions so that the sheet surface is flexed against the concave body surface.

A further object is to incorporate the foregoing concepts in an apparatus for photographing the image appearing on the sheet. More specifically, it is intended now to provide a sheet support which maintains the sheet so that it can be held taut or, alternatively, flexed against the body surface, combined with a support for a camera and a source of illumination.

These and other objects will be apparent from the following specification and drawings in which.

Figure 1:
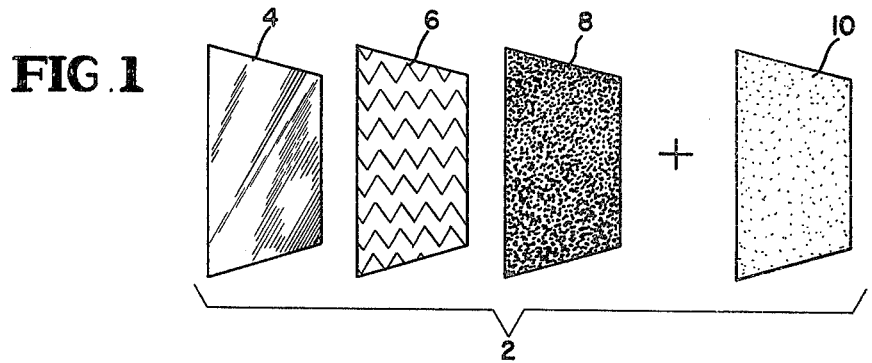
FIG. 1 is an exploded isometric view of a topical thermographic sheet assembly.
Figure 2:
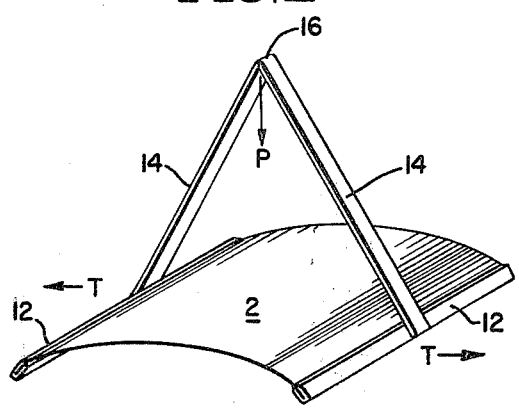
FIG. 2 is a perspective view of a topical thermographic sheet and a sheet support.

Referring now to the drawings in which like reference numerals denote similar elements, FIG. 1 diagramatically illustrates, in exploded view, a thermographic sheet 2 comprised of a flexible plastic substrate 4 having a microcapsule coating 6 thereon which, in turn, has a black coating 8. The exterior of black coating 8 may be provided with a protective film 10. Sheets of this type are well known in the art and the lamina may be either discrete films, or some or all may be coatings. FIG. 2 illustrates the sheet holder for applying the sheet with uniform pressure against a convex body surface. Opposite edges of sheet 2 are engaged by clamps 12 connected to spring arms 14 which, in this embodiment, are in "V"-configuration, the arms 14 being joined at 16 at the crotch of the "V". When sheet 2 is pressed against a body surface in the direction denoted by the arrow P, oppositely outward tensile forces as denoted by the arrows T result so that the sheet 2 is wrapped around a body surface, and various portions of the sheet surface are pressed uniformly against the opposing body surfaces.

Figure 3:
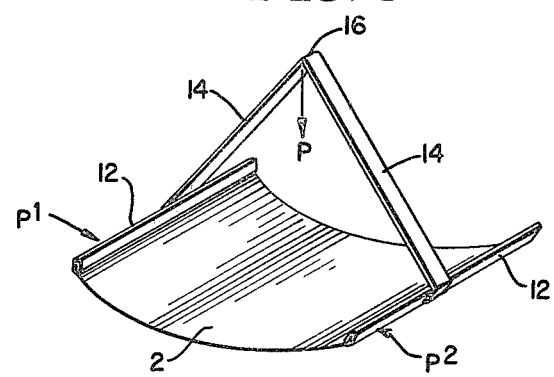
FIG. 3 is a view similar to FIG. 2 but showing the sheet maintained in flexure.

FIG. 3 illustrates the invention as utilized for applying sheet 2 with uniform pressure against a concave body surface. In this example, sheet 2 is bowed or flexed outwardly so that when it is pressed against a concave body surface, inwardly directed compression forces P1, P2 result.

Figure 4:
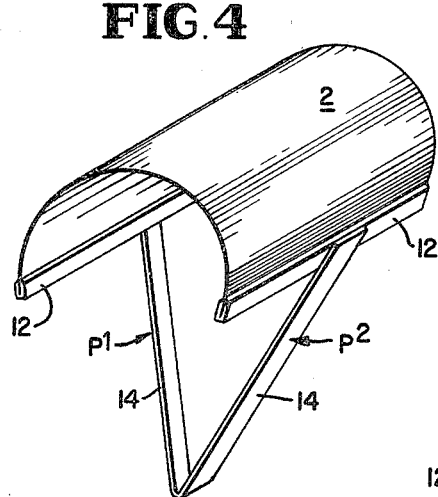
FIG. 4 is a view similar to FIGS. 2 and 3 but showing the sheet supported so that it can be wrapped around a body member.

FIG. 4 illustrates the use of the embodiment of FIG. 3 for wrapping the sheet around a body member. In this instance, sheet 2 is flexed outwardly, as in the FIG. 3 embodiment, but the body member is placed within the concavity of the sheet.

Figure 5:
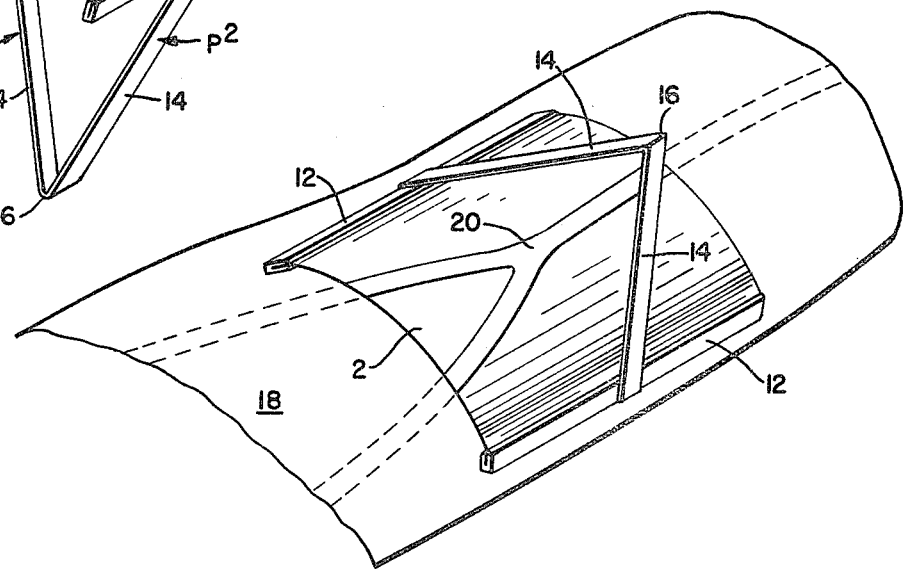
FIG. 5 is a view similar to FIG. 2 showing the sheet applied over a convex body surface.

FIG. 5 illustrates the application of the FIG. 2 embodiment onto an arm surface 18 for observing the temperature of a vessel 20. Under certain conditions it may be preferable to utilize an elastic strap connected to clamps 12 for wrapping the sheet tightly against the arm surface.

Figure 6:
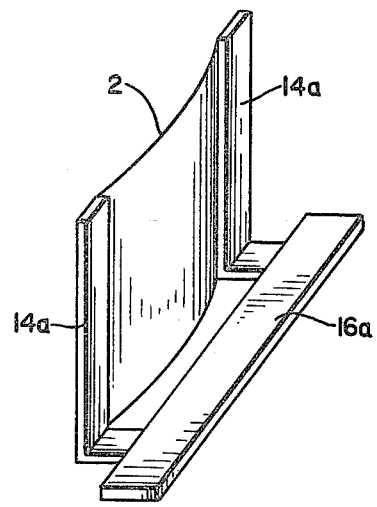
FIG. 6 is a perspective view of a modified form of sheet holder.
Figure 7:
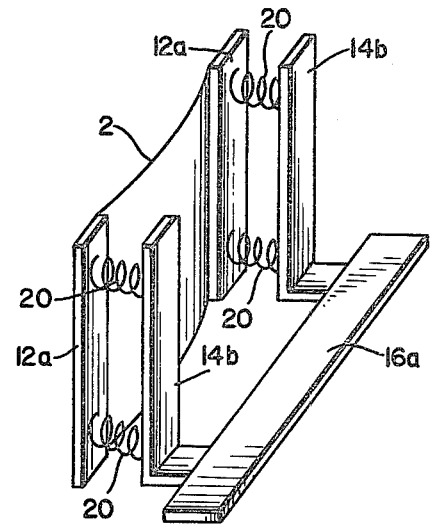
FIG. 7 illustrates a further modification of the sheet holder of FIG. 6.

FIG. 6 illustrates another form of sheet holder wherein the opposite edges 2 of the sheet are clamped by elongate spring arms 14a which, together with a crossbar 16a form a "U". A further modification of the FIG. 6 embodiment is shown in FIG. 7 wherein the clamps 12a along opposite edges of sheet 2 are supported on upstanding arms 14b by compression springs 20. In both the FIGS. 6 and 7 embodiments it is noteworthy that the crossbar 16a which supports the arms 14a or 14b is out of the range of vision of the observer or, as will be apparent from FIG. 8, a camera used for photographing the image on the sheet.

Figure 8:
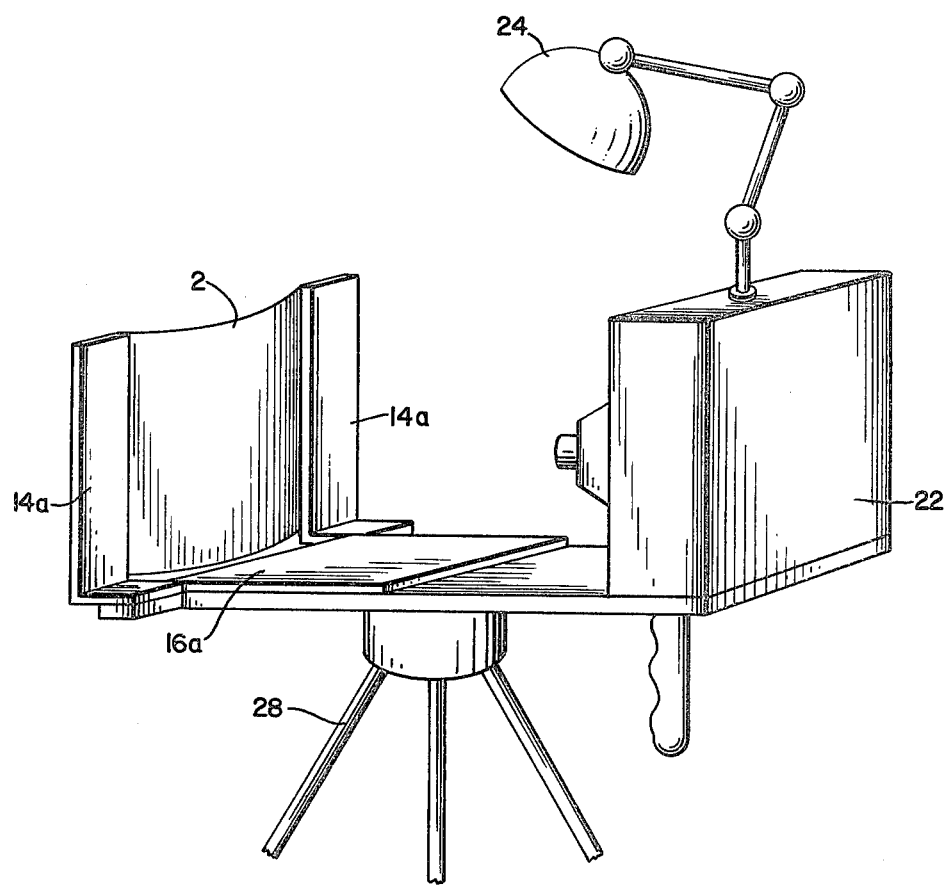
FIG. 8 is a perspective view of a sheet holder constructed according to FIG. 6 together with a camera support.

FIG. 8 illustrates a camera set-up. Opposite edges of sheet 2 are clamped by spring arms 14a which stand upwardly from the platform 16b which constitutes the cross member corresponding to crossbar 16a. A camera mount 22 at the other end of platform 16b may be provided with a source of illumination, for example, the flash illuminator 24.

Figure 9:
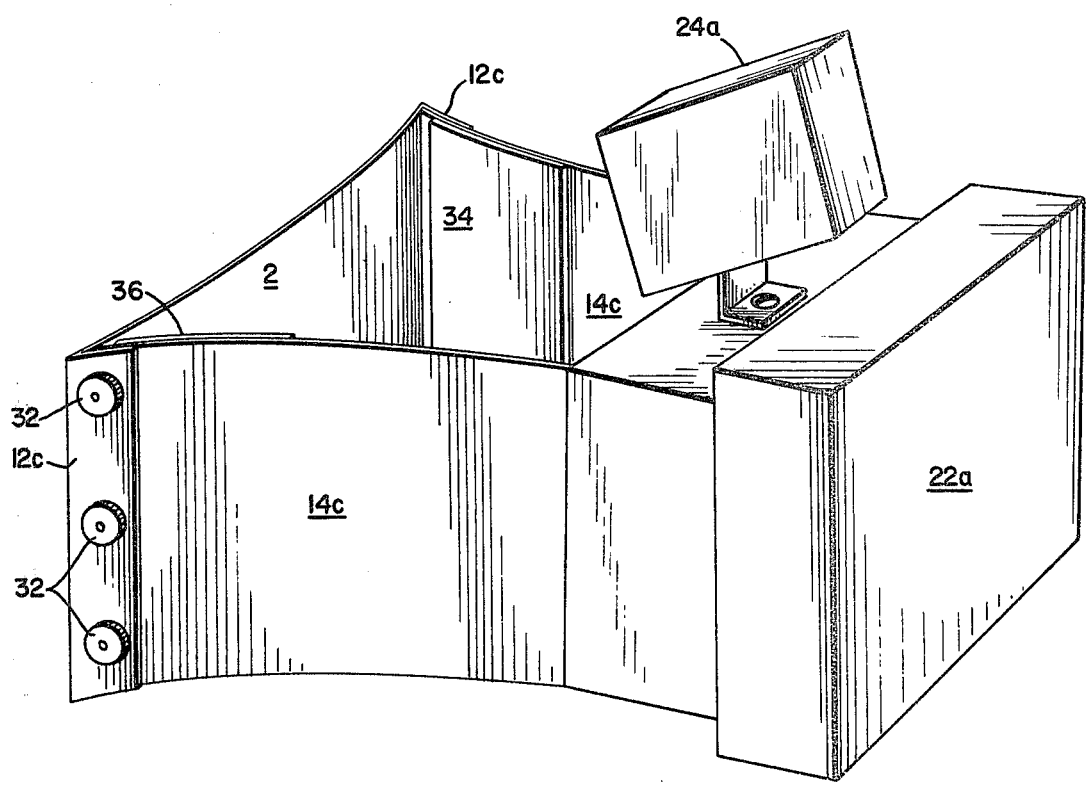
FIG. 9 is a perspective view illustrating another sheet holder adapted especially for use with a camera with provision for facile replacement of the sheets.
Figure 10:
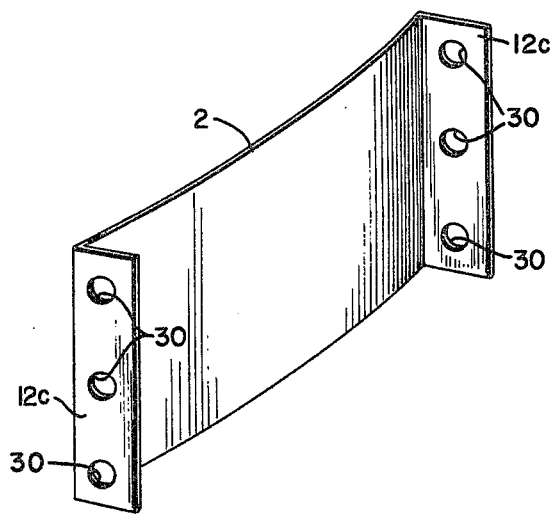
FIG. 10 is a perspective view illustrating a sheet adapted for use with the FIG. 9 apparatus; and, FIG. 11 is a plan view of the FIG. 9 embodiment.
Figure 11:
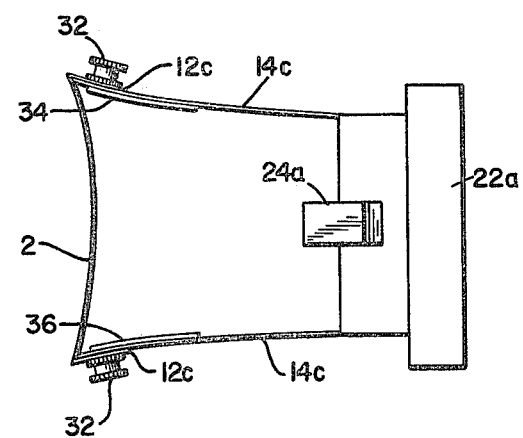

FIG. 9 illustrates a modified form of camera set-up wherein the clamps 12c along opposite edges of sheet 2 are constituted by strips which have screw holes 30 so that they may be readily attached by thumbscrews 32 to the free ends of the spring plates 14c which, in this instance, constitute the spring arms that stretch the sheet taut against a body surface. In this example the spring plates 14c shield the sides of the space between the camera 22a and sheet 2. The flash illuminator 24a may be mounted over the camera support 22a. Mirrors 36 along side the outer extremities of the spring plates may be used for improving the edge-field.

I claim:

1. Topical thermographic apparatus comprising a flexible sheet of thermographic material having a myriad of closely-adjacent sites which respond chromatically according to variations in temperature and being adapted to be engaged against a body surface (for displaying variations in color characteristic of various temperatures along the body surface,) and sheet-edge engaging means for applying opposing forces across the sheet in response to force against the surface of the sheet, whereby to maintain substantially uniform pressure of the sheet surface against those portions of a body surface against which the surface of the sheet is pressed.

2. Topical thermographic apparatus as defined in claim 1, said sheet-edge engaging means comprising a spaced pair of clamps connected by spring means.

3. Topical thermographic apparatus as claimed in claim 2, said spring means including a pair of spring arms each having one end thereof connected to one of said clamps and a connection between the other ends thereof.

4. Topical thermographic apparatus as claimed in claim 3, said spring arms and connection being in substantially "V"-configuration with the clamps connected to divergent end portions thereof and the connection between the other ends thereof being between their convergent ends.

5. Topical thermographic apparatus as claimed in claim 3, said spring arms and connection being in substantially "U"-configuration with the clamps connected along the arms of the "U", the connection between the other ends comprising a crossbar, a frame having laterally spaced portions, said crossbar being mounted on one frame portion with the spring arms extending upwardly therefrom, and a camera mounted on the other portion of the frame arranged to photograph an image on the sheet.

6. Topical thermographic apparatus is claimed in claim 3, said connection including camera means spaced from the flexible sheet and disposed for photographing an image on said sheet.

7. Topical thermographic apparatus is claimed in claim 6, said spring arms comprising a pair of flexible plates providing shrouds on opposite sides of the space between said camera means and the flexible sheet.

8. In topical theremographic apparatus as claimed in claim 7, a source of illumination disposed to project light on the flexible sheet from the general direction of said camera means, and mirror means on the flexible plates for reflecting the light from the source of illumination onto the flexible sheet.

* * * * *